(12) United States Patent
Raghavan et al.

(10) Patent No.: US 12,357,274 B2
(45) Date of Patent: Jul. 15, 2025

(54) SYSTEMS AND METHODS FOR ACQUIRING ULTRASONIC DATA

(71) Applicants: Raghu Raghavan, Baltimore, MD (US); Timothy Poston, Bangalore (IN)

(72) Inventors: Raghu Raghavan, Baltimore, MD (US); Timothy Poston, Bangalore (IN)

( * ) Notice: Subject to any disclaimer, the term of this patent is extended or adjusted under 35 U.S.C. 154(b) by 153 days.

(21) Appl. No.: 17/932,168

(22) Filed: Sep. 14, 2022

(65) Prior Publication Data

US 2023/0017291 A1 Jan. 19, 2023

Related U.S. Application Data

(63) Continuation-in-part of application No. 16/144,536, filed on Sep. 27, 2018, now abandoned, which is a continuation of application No. 14/568,138, filed on Dec. 12, 2014, now Pat. No. 10,231,704.

(60) Provisional application No. 62/040,007, filed on Aug. 21, 2014, provisional application No. 61/918,664, filed on Dec. 20, 2013.

(51) Int. Cl.
*A61B 8/00* (2006.01)
*G06T 7/00* (2017.01)
*G16H 40/00* (2018.01)

(52) U.S. Cl.
CPC ............. *A61B 8/46* (2013.01); *A61B 8/4245* (2013.01); *A61B 8/4254* (2013.01); *A61B 8/461* (2013.01); *A61B 8/483* (2013.01); *A61B 8/52* (2013.01); *A61B 8/5207* (2013.01); *A61B 8/5223* (2013.01); *A61B 8/565* (2013.01); *G06T 7/0012* (2013.01); *G16H 40/00* (2018.01)

(58) Field of Classification Search
CPC ............... A61B 8/4245; A61B 8/4254; A61B 8/461–469; A61B 8/48–5292; A61B 8/54–546; G01S 15/8906; G01S 15/895–8956; G01S 7/52036
See application file for complete search history.

(56) References Cited

U.S. PATENT DOCUMENTS

| | | | |
|---|---|---|---|
| 7,758,509 B2 | 7/2010 | Angelsen et al. | |
| 8,348,846 B2 | 1/2013 | Gunther et al. | |
| 8,630,867 B2 | 1/2014 | Yoo | |
| 2005/0228276 A1 | 10/2005 | He et al. | |
| 2005/0240103 A1* | 10/2005 | Byrd | G01S 7/52033 600/437 |
| 2007/0167705 A1 | 7/2007 | Chiang et al. | |
| 2007/0239004 A1 | 10/2007 | Kakee et al. | |
| 2009/0169074 A1 | 7/2009 | Avinash | |
| 2009/0299175 A1 | 12/2009 | Bernstein et al. | |
| 2010/0121156 A1 | 5/2010 | Yoo | |

(Continued)

OTHER PUBLICATIONS

Hsu et al., "Freehand 3D Ultrasound Calibration: A Review, Cued/F-Infeng-TR 584", University of Cambridge, Department of Engineering, pp. 1-30, Dec. 2007.

(Continued)

*Primary Examiner* — Carolyn A Pehlke
(74) *Attorney, Agent, or Firm* — DLA Piper LLP (US)

(57) ABSTRACT

Methods and systems for obtaining and reconstructing imaging data are disclosed. The methods and systems can comprise: receiving signals; storing pixel locations for the received signals; computing parameters from the received signals and pixel locations; optimizing the parameters; and performing optimized reconstruction of the images.

24 Claims, 6 Drawing Sheets

(56) References Cited

U.S. PATENT DOCUMENTS

| | | |
|---|---|---|
| 2010/0179428 A1 | 7/2010 | Pedersen et al. |
| 2011/0190629 A1 | 8/2011 | Guenther et al. |
| 2012/0238875 A1 | 9/2012 | Savitsky et al. |
| 2012/0243757 A1 | 9/2012 | Funka-Lea et al. |
| 2013/0065211 A1 | 3/2013 | Amso et al. |
| 2013/0237811 A1 | 9/2013 | Mihailescu et al. |
| 2013/0296707 A1 | 11/2013 | Anthony et al. |
| 2013/0317365 A1 | 11/2013 | Anthony et al. |
| 2014/0004488 A1 | 1/2014 | Tepper et al. |
| 2014/0058261 A1* | 2/2014 | Ichioka ............... A61B 8/54 600/440 |
| 2015/0320399 A1 | 11/2015 | Chono et al. |
| 2020/0364854 A1* | 11/2020 | Fedewa ............... G06T 7/0012 |

OTHER PUBLICATIONS

Rohling, "3D Freehand Ultrasound: reconstruction and Spatial Compounding", Churchill College, Department of Engineering, pp. 1-158, Sep. 1998.

Banker et al., "Interactive Training System for Medical Ultrasound", 2008 IEEE International Ultrasonics Symposium Proceedings, 978-1-4244-2480-1/08, pp. 1350-1354 (2008).

Website: http://kpiultrasound.com/4D-ultrasound-machines/View-all-products.html, retrieved Dec. 12, 2013.

Fenster et al., "Three-Dimensional Ultrasound Imaging", Phys. Med. Biol., vol. 46, pp. R67-R99 (2001) (www.iop.org/Journals/pb PII: S0031-9155(01)12089-0).

Goldsmith et al., "An Inertial-Optical Tracking System for Portable, Quantitative, 3D Ultrasound", 2008 IEEE International Ultrasonics Symposium Proceedings, pp. 45-49 (2008).

International Search Report issued in PCT/US2014/069862 dated Apr. 13, 2015.

Written Opinion issued in PCT/US2014/069862 dated Apr. 13, 2015.

International Preliminary Report on Patentability issued in PCT/US2014/069862 dated Jun. 21, 2016.

Indian Office Action issued in Application No. 201617023493 dated Jul. 8, 2020.

\* cited by examiner

SYSTEMS AND METHODS FOR ACQUIRING ULTRASONIC DATA

RELATED APPLICATION DATA

This application is a Continuation in part to U.S. application Ser. No. 16/144,536 filed on Sep. 27, 2018, which is a continuation of U.S. patent application Ser. No. 14/568,138, filed Dec. 12, 2014, which claims priority from U.S. Provisional Patent Application Ser. No. 62/040,007, filed 21 Aug. 2014, and U.S. Provisional Patent Application Ser. No. 61/918,664, filed 20 Dec. 2013. All of the forgoing are incorporated by reference herein in their entireties.

DESCRIPTION OF EMBODIMENTS OF THE INVENTION

Ultrasound imaging is a procedure used in a wide variety of conditions (e.g., examination of fetal and maternal health during pregnancy). In addition, high quality ultrasound scanning equipment that can be attached to personal devices such as smartphones and tablets can allow widespread dissemination of scanning technology (e.g., in remote and rural areas). Various procedures can be used for training personnel, both in the acquisition of images with hand-held ultrasound transmitters, and in analyzing them for diagnostic as well as metric purposes.

Musculoskeletal pain and/or discomfort can be associated with scanning for ultrasound imaging. Any area of the body, including but not limited to the neck, shoulder, wrist, hand, fingers, and/or back can be areas where pain is reported. For example, the following activities can aggravate pain and discomfort: manipulating the transducer while sustaining applied pressure, shoulder abduction, and/or sustained twisting of the neck/trunk.

Figure 1A:
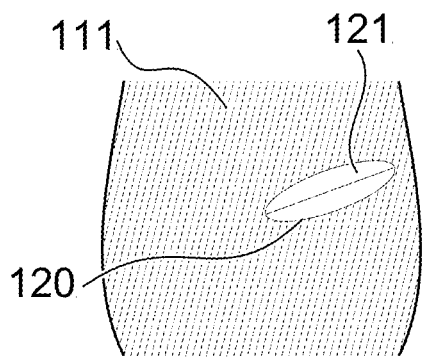
FIGS. 1A and 1B illustrate an example constraint on the position of an ultrasound probe in the prior art.
Figure 1B:
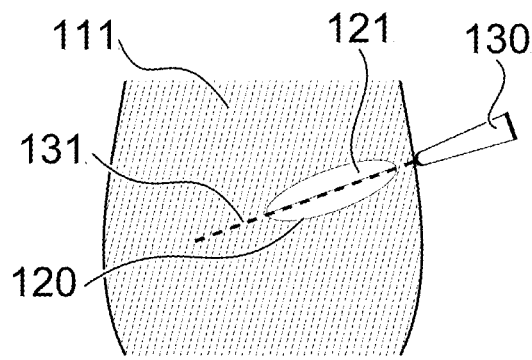

FIGS. 1A and 1B illustrates a body 111 that contains an organ 120, in which there is an elongated structure 121 for which a clinician needs to obtain an image. For example, the blood vessels of the liver in a patient may need to be displayed lengthwise in order to obtain the required image. The standard technology of ultrasound emits signals as rays 131, along which echoes return and allow creation of an image by the ultrasound probe 130 and the associated software.

For a single ray, the amplitude of the echo may be plotted against a return time (e.g., implicitly against distance) in an 'A-scan' with peaks at strong echoes. In other embodiments, a planar set of rays can be compounded into a 2D image, with echo strength shown as brightness (e.g., called 'B-scan'), referred to here as a 'slice'. The probe 130 can also be in contact with the body, and in contact with it via an impedance-matching gel. This can require a specific position and angle for the probe (e.g., including a specific 3D rotation about its axis), except that the probe may move a little sideways within its required acquisition plane. Each single image can require a specific position and angle for the probe, guided by the operator's view of the display which can show the image currently acquired. This guidance can require the operator to have an intimate familiarity with anatomy, which can make training long and arduous. It can also require the hand holding the probe to bend at the wrist in the appropriate way to hold the probe at the various precise angles required. The arm and the shoulder may need to be used to reach across from where the operator is watching the display. The stress and tension can be continuous, for hours on end, as the need is urgent and qualified operators may not meet the need.

Furthermore, the need for substantial human intelligence in the acquisition process can make it difficult to apply machine intelligence to the result. The radiographer is, of course, aware of the anatomical surroundings of the plane currently displayed (e.g., "how the plane was found"). These anatomical surroundings, however, are not explicitly in the data from the probe. Artificial Intelligence (AI) solutions have also been employed to help guide a user to acquire diagnostic images (Muse, E. D., and Topol, E. J. (2020). Guiding ultrasound image capture with artificial intelligence. *The Lancet* 396 (10253), 749), but these must be trained and tailored to each specific procedure and still require some level of skill in understanding ultrasound images to guide the transducer to the correct vicinity. AI can also be subject to population, transparency, equity, and economic bias issues and, more recently, "model drift" has been shown to affect outcomes (Lacson, R., Eskian, M., Licaros, A., Kapoor, N., & Khorasani, R. (2022). Machine Learning Model Drift: Predicting Diagnostic Imaging Follow-Up as a Case Example. *Journal of the American College of Radiology*). 3D ultrasound can potentially solve the issue of guidance by enabling a user to capture the organ volume and thereby permitting a remote radiologist to capture the desired image planes through multiplanar reformation.

Figure 2A:
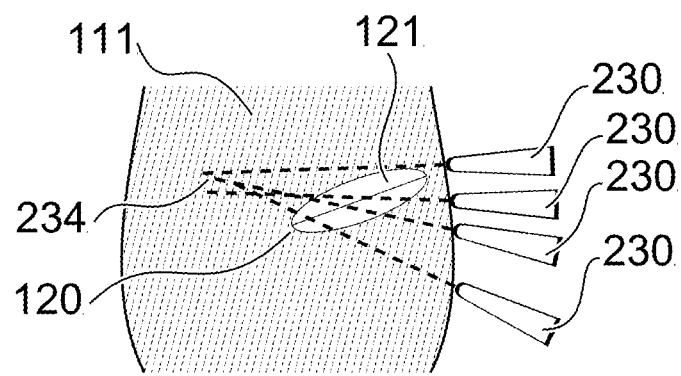
FIG. 2A illustrates a less-constrained cloud of positions for an ultrasound probe, according to embodiments of the present invention.
Figure 2B:
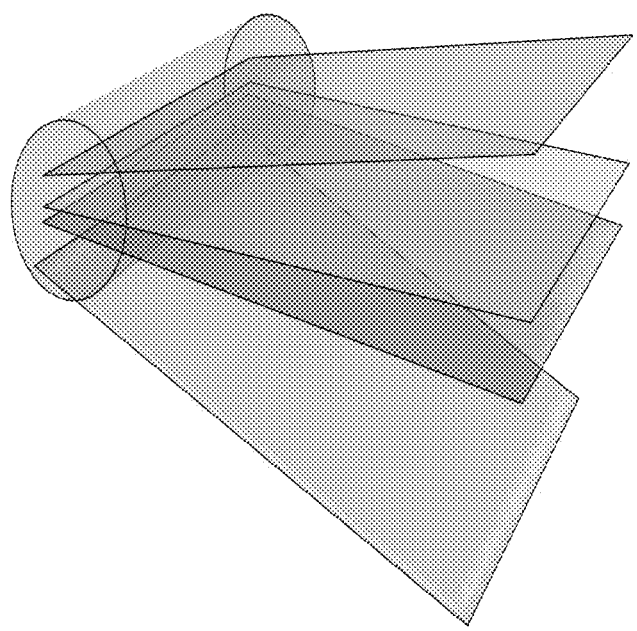
FIG. 2B illustrates a scanner used in "B-mode" that acquires planes of data which have to be positioned accurately relative to one another for proper reconstruction.

Embodiments of the invention can replace the requirement for specific, narrowly defined positions of the probe by allowing the probe to be held, as shown in FIG. 2A, moving through a variety of positions 230, with no specific angular requirements on individual 2D images. The rays echoed, considered in their totality 234, may only be required to cover a 3D volume including the organ 121. Graphical cues can indicate to the operator whether this has been achieved. From this information, and position data for each ray, a volume data set can be built. This volume data set can be volume rendered as a 3D image, and inspected in any 2D cross-section, rather than those originally acquired 2D cross-sections at specific moments, by computationally re-slicing as needed. The risk of musculoskeletal disorder can be reduced for the operator because of the greater flexibility allowed in positioning the probe, and can also be reduced for the clinical examiner (who may not need to work at the same time, or even be the same person) by the fact that the volume data can be revolved, unlike the patient. The wrist and hand of the sonographer, using a device such as a mouse, can thus remain in comfortable positions.

By assembling a volume data set, we can make the data independent of the viewpoint and angle, so that automating tasks such as (a) identifying the prostate, and (b) establishing whether it is enlarged, become practical. The invention thus can comprise supplying such data to diagnostic algorithms, using only a 2D scanner.

FIG. 2A illustrates how the operator can move the probe freely 230 over the patient, aiming only to cover a certain target volume. The probe can include a tracker of its position with respect to six degrees of freedom (e.g., such as side-to-side, up-and-down, far-and-near, roll, pitch and yaw, or equivalent descriptions well known to those skilled in the art). This tracker may be electromagnetic (e.g., Polhemus™, Ascension™, etc.), inertial sensors (IMU) (e.g., TDK InvenSense ICM-20948, ST Micro LSM9DSI 9-Axis iNemo inertial module), optical by camera view of landmarks on the probe, optical by cameras mounted on the probe and observing fixed landmarks, or any other system that can deliver sufficient precision (e.g., with errors at most 1 mm in location, 1° in angle). Some probes that may be employed, such as, but not limited to: Clairus C3 HD3 MultiPurpose Scanner, Philips Lumify C5-2 Curved Array Transducer, or Interson GP-C01.

Figure 2C:
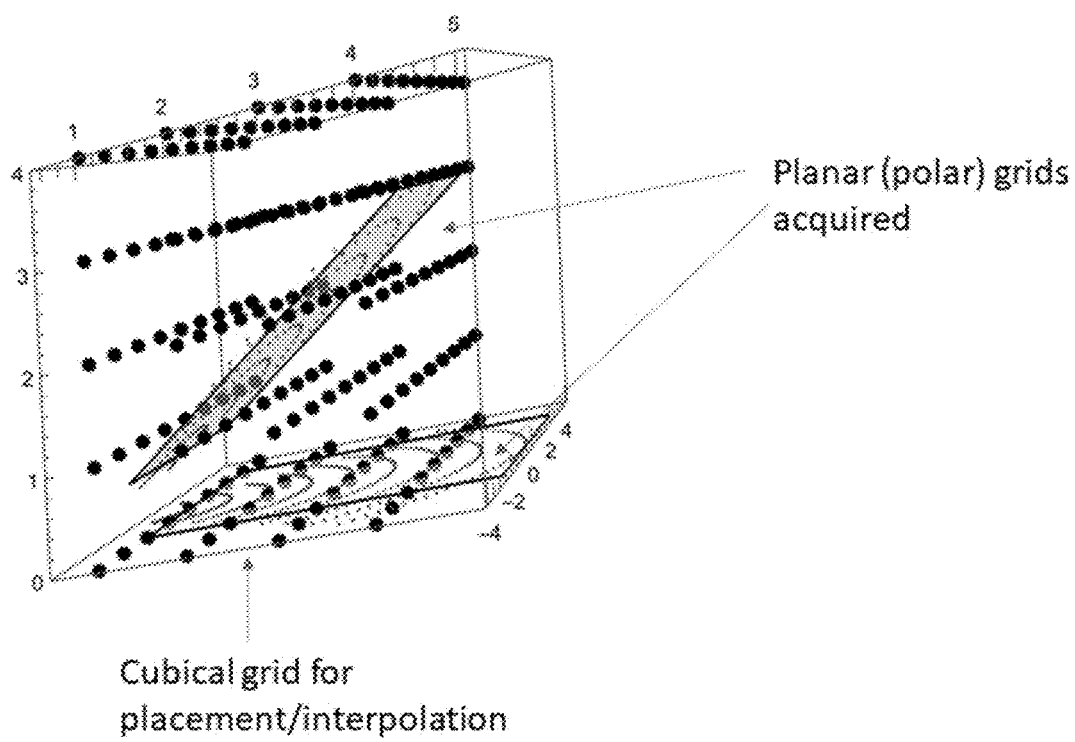
FIG. 2C illustrates how the scanner obtains a polar grid arrangement of pixel values which have to be interpolated and reconstructed into a 3D grid of voxel values.

In some embodiments, a difficulty with the IMU sensor may be the inaccuracy of the translational measurement, which may depend as it does on accelerometers. In order to position the planes an origin in three dimensions and the orientation, comprising six parameters for each plane, relative to say the first one may be needed. FIG. 2C shows how planes can be positioned in space, in accordance with the readings from the tracker. Due to inaccuracies, the relative positioning of these planes may be in error. However, current IMU's can include magnetometers and the orientational accuracy requirement mentioned above can generally be met. It is the translational measurement that may need to be corrected. However, since each position measurement is associated with an image capture and the imaging region is oversampled, we can attempt to correct the position data by correlating the image data. This approach could be applied directly to the image data by comparing each captured image to the corresponding oblique plane in the reconstructed volume using a particular measure of goodness of fit such as least squares deviation or mutual information. The positional parameters could then be iteratively adjusted to optimize the fit of the entire image set.

A method here disclosed can use a statistical signal model to provide the optimal solution: further, such an approach can lend itself to continual improvement based on data and machine learning. A standard model for the complex analytic signal S in B-mode ultrasound (e.g., Wagner, R. F., Insana, Michael F., and Smith, Stephen W. (1988). Fundamental Correlation Lengths of Coherent Speckle in Medical Ultrasonic Images. *IEEE Transactions on Ultrasonics, Ferroelectrics, and Frequency Control* 35(1), 34-44, which is herein incorporated by reference) can show, to a good approximation, that it is a sample from a complex Gaussian process with zero mean, and hence can be completely characterized by its covariance function. For clarity, let us use u to denote a point in probe-fixed coordinates in the plane scan sector, i.e., it is a two dimensional vector. Then the covariance may be written as (loc. cit, eqn(3), but in our notation) can be written as follows:

$$\langle S(u_1,E_1)S(u_2,E_2)\rangle \approx \rho(\circ)\int d^3X\, P(u_1,E_1,X)P^*(u_2,E_2,X).$$

The symbol $\rho$ can stand for a slowly varying energy reflectivity assumed to be constant over the region imaged, which can have the volume of the support of the functions P. In turn P may be calculated if we know the point-spread function h of the ultrasonic probe, including both transmission and reception and the beamforming therein and the transformation E. In fact, $P(u, E, X)=h(u, Ex)$. This function may be well-characterized and may be assumed known. In the above, the angle brackets denote the expected value which may vanish unless the two 'points' imaged are in the overlap of the point spread functions. Then, the omitted argument of the slowly varying r can be taken to be either of these points, both being close to the X's involved in the integration.

Optimal estimation of E near the inaccurately reported values can be deduced with either maximum likelihood estimation (MLE) or, with a model for the positional errors of the IMU, can be generally available from the manufacturer, further measurable by, for example, calibration against an accurate EM sensor, with potentially maximum a posteriori (MAP) Bayesian estimates. In fact, both E and r may be simultaneously estimated thus building a better reconstruction. Estimates of the parameters, be they the locations or the echogenicities, can be close to the true value, so that gradient descent may be a fast way to maximize the probabilities.

An alternative to adequately correcting all of the positional errors from the IMU is to mitigate the issue if it arises by providing additional acquisitional guidance to the user. The operator could be directed to recalibrate periodically if calibration fits became inaccurate due to drift. Furthermore, these sensors may be more accurate at orientation measurements and can correct for orientation drift using its magnetometer. Thus, the operator could be directed to obtain rotational sweeps at fixed locations so that most of the positional variation is rotational.

An additional position may be the design with the frame as described in: Herickhoff, C. D., Morgan, Matthew R., Broder, Joshua S., and Dahl, Jeremy. (2017). Low-cost Volumetric Ultrasound by Augmentation of 2D Systems: Design and Prototype. *Ultrasonic Imaging*, 1-14) and in (Morgan, M. R., Broder, J. S., Dahl J. J., and Herickhoff, C. D. "Versatile Low-Cost Volumetric 3-D Ultrasound Platform for Existing Clinical 2-D Systems," in *IEEE Transactions on Medical Imaging*, vol. 37, no. 10, pp. 2248-2256 October 2018, doi: 10.1109/TMI.2018.2821901 (which is herein incorporated by reference).

Interpolation between grids: Even after the correct placement of acquired scan planes, a further problem to be solved may be that illustrated in FIG. 2C. The heavy black dots can be the positions of voxels arranged in a cubical grid (shown in a perspective projection). The lighter dots arranged along circular paths can be the pixels naturally acquired by the probe. We denote the collection of signal values obtained from the scan planes of the probe as S2 and those placed in a cubical grid as S3. An example method for interpolating S2 into S3 is a trilinear or similar interpolation of the B-mode values themselves. Other methods known in the art may also be used.

An example method disclosed herein is to work with the complex signal again, obtained from the RF signals. As noted above, these may be jointly Gaussian random variables with zero mean, and the MLE may be constructed to estimate S3 values, given the values S2 in the planar, perhaps also polar, grids. Such an estimator may be optimal from the probabilistic point of view (e.g., values of S3 given the data at hand) and may be expected to be superior to the current interpolation methods which do not account for the signal model at all. Note that this signal reconstruction algorithm may be independent of the position estimation one above, though they both exploit the Gaussian model for the complex signal resulting from speckle statistics.

The tracked positions can serve a dual purpose: (1) They can allow the data from each ray to be connected to particular points in a common coordinate system. The echoes from each of those points can be interpreted as ultrasound reflectivity at that point. Thus, a data set giving the reflectivity at each point in a volume can be accumulated in a 3D scan format (e.g., in CT or MRI), and displayed and examined by arbitrary slicing, volume rendering, etc., as is commonly done with such data.

Figure 3:
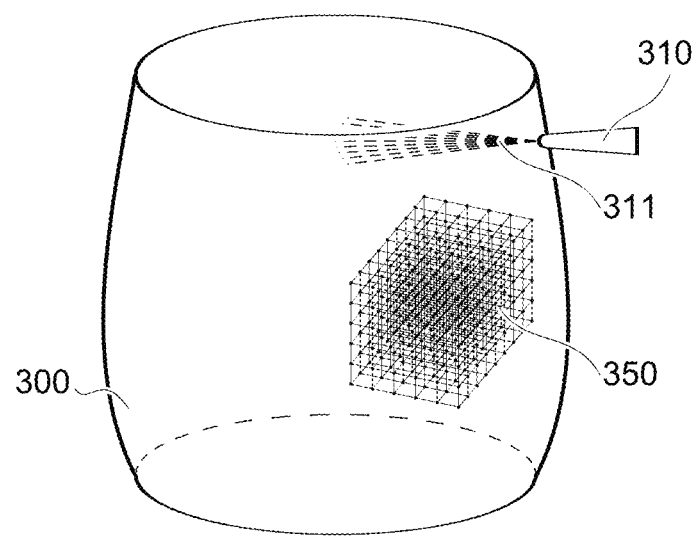
FIG. 3 illustrates a display of the target region in the context of the body, for the purpose of aiming the probe, according to embodiments of the present invention.

(2) By beginning the scan by touching fiducial points on the surface of the patient, the position of the patient's body can be related to the same common coordinate system. (See, for example, detail provided with reference to FIG. 5.) Thus a display (e.g., as shown in FIG. 3) can show the position of the probe 310 and the rays 311 along which the probe 310 is currently emitting ultrasound in relation to the body 300. The body is shown as a graphical model of the surface, previously stored. It can adapt its form to such patient data as sex, height, body mass index (BMI) and the positions of the fiducials. (For example, the navel is an easily identified fiducial: the more it is in front of the other fiducials, the larger the belly relative to the patient.) This can enable the computer to estimate the position of a particular tissue, such as the liver or a kidney, and display a volume 350 that includes it. It can optionally display a graphic of that tissue, in the estimated position. But is can also display a covering volume, with a margin allowing for variability between patients' internal anatomy.

Thus, the operator can see where the fan 311 of rays that the probe 310 is currently emitting, relative to the target volume, without referring to the echo data that it returns. The computer can test the returned data for problems (e.g., noise, shadowing, artifacts). If it passes these tests: (1) it can add the reflectivity data to the points within a small radius of the rays' positions, (2) it can label those points as 'touched', and (3) it can modify the display of the target volume. In an example modification (e.g., FIG. 4) the volume is first shown in 400 as an untouched array of identically colored dots 401.

This can resemble the computational volume, an array of echo values E[i][j][k] where the coordinates i, j, k range from 0 to L, M and N respectively in equal small steps in three orthogonal directions. (An irregular volume can be handled by the same computationally convenient cuboidal shape, by pre-loading the 'good data acquired' tag at points where no data are required.) However, it is not necessary to include all the points in the display, which may show only every nth point in each direction. A displayed 'representative' point $(i_0, j_0, k_0)$ can then be labeled as 'touched' only when good data have been acquired for every point (i,j,k) such that $$|i-i_0| \le n/2, |j-j_0| \le n/2, \text{ and } |k-k_0| \le n/2.$$

Many alternative displays of the volume can be used the art, but in some embodiments, this 'see-through' array can be effective. The dots may be 'lit' from a particular direction for additional depth cues, and joined by lines 402, to enhance the visual sense of depth. When all those points of the volume that are nearest to a particular displayed dot have been "touched", the dot can change color, or shape, or visibility, or indicate the "touching" in any other manner.

Figure 4:
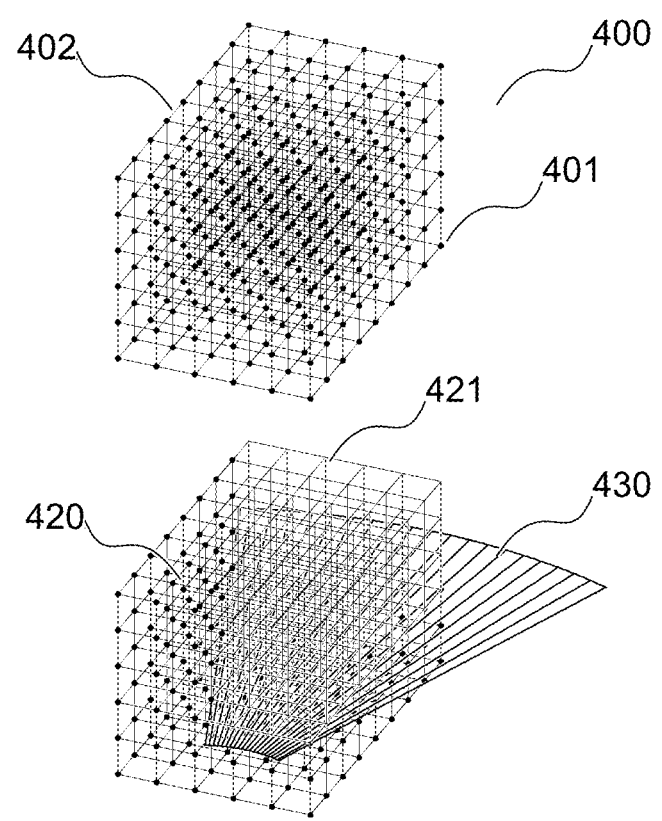
FIG. 4 illustrates feedback given to the operator on the acquisition progress, according to embodiments of the present invention.

Visibility is an option illustrated in FIG. 4. The graphic representation 430 of the fan 311 has passed downward through the region 421, changing the dots there to invisible. Below it, and in the region 420 that it has not passed through, the dots remain unchanged. To complete the scan of the target volume in this case, at least one more sweep of the fan may be needed. With a smaller target, a single sweep could suffice.

Alternatively, every point in the array may be considered representative of itself. These may be too numerous for individual graphic representation, and can be shown by a method of volume rendering such as ray casting, where 'touched' points become transparent. This may be supplemented by lines showing the outline of the volume.

In some embodiments, the operator may not need to have an in-depth understanding of human anatomy, beyond the placement of fiducials at certain points (e.g., the navel). There may not be a need to keep the successive fans of acquisition parallel, as in CT and MRI scans, or avoid crossing: by the position tracking described above, the computer maps them into a common space. They must be sufficiently close to the previous and next fan positions to avoid gaps larger than the imaging resolution. A point left out is not 'touched' and must be revisited, as the display will show by the nearest dot remaining unaltered. Jerky motion can produce detectable motion artifacts, and similarly unaltered dots. A smooth, unhurried motion may require the least re-sweeps.

Where there is evidence of shadowing (e.g., a bright point such as a reflective bone, a dim point such as a kidney stone) these points (e.g., even if they are outside the target volume) can be mapped and showed in the display. This can guide the operator in aiming the fan past or between such structures, and completing the scan.

This mode of operation can require less training than an anatomy-guided ultrasound. It can also be more permissive on actions with the probe (e.g., by wrist position), and thus can cause less musculoskeletal stress to the operator. It can also be faster for some operators, because a few loosely aimed sweeps can suffice to scan a problem tissue. This can reduce the workload of individual operators.

The neck and shoulder stress that can be common causes of disorder can be caused from the ergonomics of looking at a screen that is off to the side of the patient. Either the operator's neck is twisted for hours to view the display, or the shoulder supports an arm that is very much off to one side.

Figure 5:
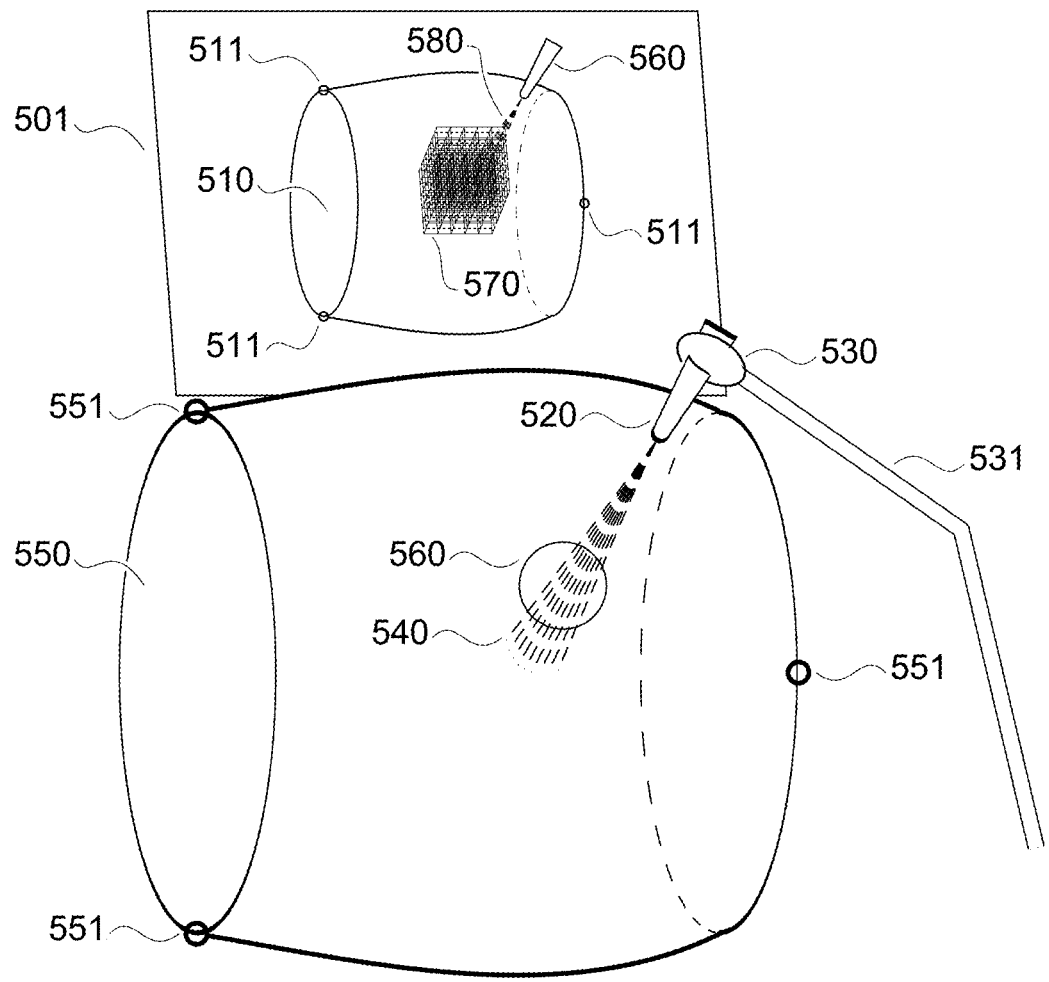
FIG. 5 illustrates the alignment of a patient with a screen display, including the fiducials by which the correspondence of patient and image is achieved, according to embodiments of the present invention.

In one embodiment, a display 501 is arranged directly beyond the patient 550. (The anatomy shown in FIG. 5 can represent any static part of the body penetrable by ultrasound.) In this way, the operator can look straight at the workpiece directly forward of the body, as shown in FIG. 5. At the beginning of the scan, the operator can enter the name of the tissue to be scanned. The display can then show an image 510 of a standard patient in a standard position, with displayed fiducials 511 appropriate to that part of the body. The operator can place physical fiducials 551 at the corresponding points on the physical body 550, and touch them with the tip of the probe 520 (e.g., not currently emitting ultrasound 540) held in the hand 530 positioned by the arm 531. The operator can click on a button or otherwise signal to the computer to record each position of the probe 520. This can enable the computer to adapt the generic shape 510 first displayed to match the patient's specific body 550, deducing an approximation to the internal location of tissues 560, the distribution of fat, and other relevant parameters. Within the spirit of the invention, modifications may comprise touching the fiducial points directly without placing physical markers there. We prefer physical fiducials, as providing a more disciplined routine that will lead to fewer errors. Additionally, a separate 3DOF, 6DOF, or 9DOF sensor, reporting in the same coordinates as used for tracking the probe 530, can used for reporting the fiducial positions. In addition, the fiducial markers can themselves be 3DOF sensors, reporting relative to the same base, or a base with a known relation to that in the probe.

The system also enables alignment of the displayed body 510 in the same orientation as the physical body 550. And the displayed probe 560 can move parallel to the physical probe 520, turning visibly in the same way, moving in parallel to it, or touching the displayed body 510 when the physical probe 520 touches the physical body 550, or any combination thereof. The system can display a graphical fan 580 corresponding to the position of the physical ultrasound rays 540, which the system may turn on automatically at this point, or when the operator commands it. The system can display a volume 570 covering a region corresponding to a target tissue 560, to be modified by passing the fan 580 through it, which the operator can achieve by moving and turning the physical probe 520 over the surface of the physical body 550, with visual feedback as in FIG. 4.

In some embodiments, the display of the body and probe can be immediately beyond the patient, in the same field of view for the operator. The operator can face the patient directly, with the work and the guiding view of the work directly in front at a convenient working distance.

In other embodiments, the display 501 may be equipped to show objects in stereoscopic 3D, using shutter glasses, different display colors and color filters for the left and right eye, or glasses-free techniques that have merits and disadvantages well known to those skilled in the art. In addition, a monoscopic display (e.g., showing the same to both eyes) can use 3D graphics in an essential way, and can provide depth cues such as a nearer object masking a farther one.

If the position of the head is tracked in 6DOF, which is a small extension of the tracking used for the probe, the display may have the depth cue of parallax (e.g., changing as the eyes move), either for a single cyclopean view from a point between the eyes, or stereoscopically as described above. The techniques for controlling the view to match position of the head may be known to those skilled in the art.

In further embodiments, Augmented Reality (AR) can be used. This may be a portable option. The operator can wear a head-mounted or other display (e.g., Magic Leap ML-2, Microsoft Hololens, Meta Oculus VR), tracked with low latency as to its position, so that as the operator's head moves the graphical display seems always to be in the same physical location, although its position in the field of view varies (e.g., moving left when the head turns right). This is an embodiment in addition to the use of a head-mounted display that displays a view independent of the position of the head and eyes (e.g., a 'head up display'). The physical body 550 can also be visible through the head-mounted display. A graphical display which stereoscopically appears at a distance from the operator can be superimposed on this view despite the absence there of a physical display. This may appear beyond the patient (e.g., like the physical display 501), or superimposed on the body 550, so that the displayed target volume 570 has an apparent position which actually covers the (invisible) physical tissue 560.

Figure 6:
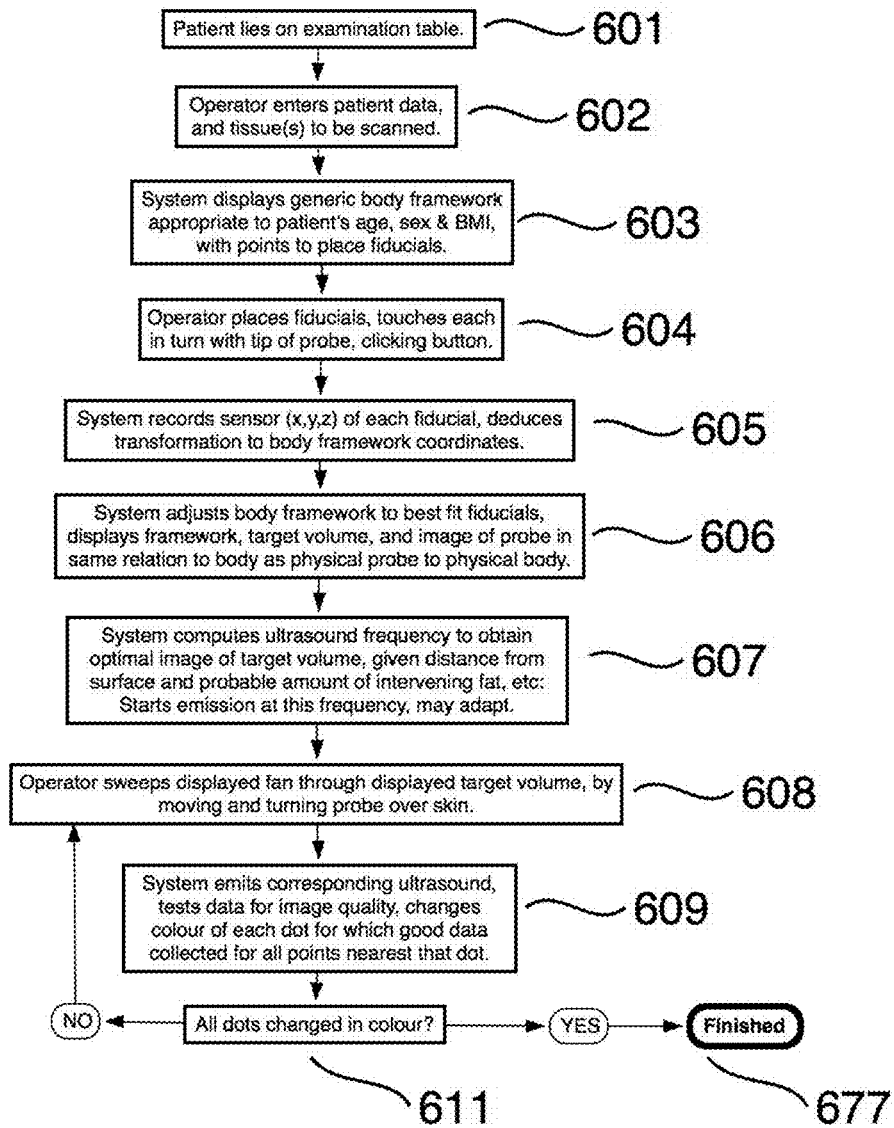
FIG. 6 illustrates a workflow of the device and operator, according to embodiments of the invention.

FIG. 6 illustrates a workflow of the operator's interaction with the system. In 601, the patient can lie on the examination table. In 602, a user (e.g., the operator, an assistant, a larger medical records system) can enter the patient's information (e.g., identity, age, sex, height and weight, and the tissue or tissues prescribed for scanning). This information can give the body mass ratio, and enable the system to deduce a first approximation to the patient's size and shape. In 603, this information can be displayed along with points 511 on the body where fiducials 551 need to be placed. In 604, the operator can place the fiducials 551 at the corresponding points 511 on the patient, mark them, and then touch them in turn with the tip of the probe, clicking a button as each is touched. (In some embodiments, an operator could simply touch the points, but explicit fiducials may provide more reliable results.) In 605, this can enable the software to relate the position reports of the position tracker built into the probe, relative to the base of the tracker, to the graphical coordinates used in the display. It can thus draw the probe in the display, showing it touching the image of the body when the physical probe touches the physical patient, and guide the operator in aiming it at the target volume. In 606, the actual positions of the fiducials enable the system to estimate more accurately the surface of the patient's body (and display it in some embodiments), the probable thickness of fat layers (which can be poorly predicted by body mass index), and/or the position within the body of the target tissue(s), which can be used to select and display the target volume. In 607, the system can set the frequency. Deep tissue can require ultrasound at a lower frequency than normal to penetrate far enough, whereas for shallow tissue, a higher frequency may need to be used for better resolution. In some embodiments, the frequency can be set according to the distance of the probe from the target, and the image quality.

In 608, the operator can use this display to guide a sweep of the displayed fan 430 through the displayed volume 400, which can cause the physical echoes of the ultrasound to return from the corresponding volume of the body, and hence the tissue selected. In 609, if these physical echoes give images of satisfactory quality, and the points from which they are returned are satisfactorily dense in a subvolume of the target volume, the dot (or any other element) representing that sub-volume can change (e.g., color). (Those of ordinary skill in the art will see that the following example measures can be used to determine whether the results are satisfactory: brightness, signal to noise ratio, entropy, Haralick textures, etc.) In 611, if unchanged dots remain, the operator can return to step 608. If all dots have changed, the scan is complete, and the process can be completed 677.

The echo data can be reorganized (e.g., locally, remotely) to an L×M×N volume image (e.g., for suitable array dimensions L, M and N), which can then be optionally transmitted to a remote location before or after the reorganization, and examined by a clinician.

These volume images can be assembled in a known relation to the estimated anatomy of the patient. It is not, of course, the exact anatomy: patients vary internally in ways that cannot be fully predicted from the relative positions of external fiducials. However, it can be estimated sufficiently well that a target volume 570 somewhat larger than the target tissue can reliably cover the range of positions that the target tissue 560 is likely to occupy. Thus, the assembled volume images can include a scan of the target tissue. Moreover, the model of the internal anatomy used to find it can be a good starting point for an adaptive model, which can be deformed to fit the actual data in the scan. If in this deformation the modeled anatomy (e.g., a prostate gland) becomes larger relative to neighboring tissues (e.g., the bladder and urethra), this can give an immediate indication of an abnormal anatomy (e.g., an enlarged prostate). Similarly, the model can adaptively identify the patient-specific shape of certain anatomy (e.g., a kidney or gall bladder), and flag abnormalities (e.g., kidney stones, gall stones). Failure to identify a sub-region with a feature of the adaptive standard map may flag the possible presence of an abnormal growth (e.g., a tumor, either benign or cancerous), or such features as a hematoma or stenosis. Machine learning techniques, given sufficient examples of scans both normal and abnormal, in the near-standard orientations provided by the scanning method and apparatus disclosed herein, and analyzed for important features (e.g., contrast, entropy and three-dimensional Haralick textures), can learn to distinguish scans showing particular abnormalities from scans of normal patients. Vessel tracing may be impossible in a planar slice, since blood vessels and other tubes twist out of any one plane. A volume dataset may allow it, so that conditions such as a vascular malformation, or the neovascularization characteristic of a growing carcinoma, may become a possible task.

In some embodiment, many types of volume analysis may be used in conjunction with the data acquisition systems and methods disclosed herein. For example, vessel tracing may be used, which may help find certain characteristics (e.g., vascular malformation, neovascularizations). (Vessel tracing may often not be possible in a planar slice because blood vessels and other tubes may twist out of any one plane.) Those of ordinary skill in the art will see that many other types of volume analysis may be used. In this way, by using a planar rather than a 3D probe, screening can be accomplished by an operator who does not need typical anatomical knowledge to conduct a scan, or typical medical knowledge to interpret it. Of course, clinical expertise may be necessary for follow-up.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112 (f). Claims that do not expressly include the phrase "means for" or "step for" are not to be interpreted under 35 U.S.C. 112 (f).

What is claimed is:

1. A method for acquiring data from ultrasonic data with a two-dimensional B-scan probe, comprising:
    a) Coupling a probe to a sensor, with a means of reporting its position in real time relative to a base;
    b) Displaying a generic body model and a set of fiducial points to be touched, in order;
    c) Deriving, from the position of the probe at each of the touches, a transformation from coordinates relative to the base to the coordinates in which the body model is defined;
    d) Deriving from the position of the probe at each of the touches an adjusted body model, with estimates of internal anatomical positions;
    e) Displaying with the adjusted body model a volume containing a target tissue, in its estimated anatomical position;
    f) Using the estimates of internal anatomical positions to estimate the absorption between the probe and its target;
    g) Using the estimate of absorption to select the ultrasound frequency and amplitude for an optimal image;
    h) Using the estimates of internal anatomical positions to estimate the speed of sound at different locations in the body, obtaining an estimate of the relation of distance to echo time;
    i) Displaying a 2D fan corresponding to the emitted sound rays in their current positions, relative to the body;
    j) Showing in representative points of the displayed volume containing a target tissue whether good data have been captured for that point;
    k) Recording the good data for each such point, in each position of the 2D fan;
    l) Assembling a volume data set from these 2D fans, filling the target volume; and
    m) Transferring the volume data set to a display accessed by a clinician.

2. The method of claim 1, wherein the sensor is an electromagnetic sensor.

3. The method of claim 1, wherein the sensor is an optical sensor.

4. The method of claim 1, wherein the sensor is an inertial sensor.

5. The method of claim 4, wherein the inertial sensor is a micro-electro-mechanical system (MEMS).

6. The method of claim 1, wherein reported values from the sensor are corrected by direct acquisition of the complex analytic signals, and optimal statistical estimation algorithms.

7. The method of claim 6, wherein the optimal statistical estimation uses the real part of the complex analytic signal.

8. The method of claim 6, wherein the reported values are corrected by image correlation and alignment methods.

9. The method of claim 1, wherein errors in reported values are mitigated by additional acquisition guidance relayed to the operator by software.

10. The method of claim 1, wherein the volume data set is automatically analyzed for abnormalities as a stage of the transfer.

11. The method of claim 10, wherein the analysis warps the standard anatomical model to best fit said volume data set, and identifies points of misfit.

12. The method of claim 10, wherein the analysis identifies tissues within the volume data set.

13. The method of claim 12, wherein the analysis reports on the dimensions of the tissues.

14. The method of claim 10, wherein the analysis is based on machine learning techniques.

15. The method of claim 1, wherein a representative point changes color or visibility when every point nearer to that point than to any other representative point has good data associate with it.

16. The method of claim 1, wherein all points in the volume are considered representative, and the collection of points without good data represented by volume rendering.

17. The method of claim 1, wherein the display is aligned with the patient and placed above or behind the patient relative to the operator.

18. The method of claim 1, wherein the display is stereoscopic.

19. The method of claim 1, wherein the display uses head tracking to provide the depth cue of parallax.

20. The method of claim 1, wherein the display is head mounted.

21. The method of claim 7, wherein the reported values are corrected by image correlation and alignment methods.

22. The method of claim 20, wherein the display shows a view of the target volume simultaneously with the view of the real body by optical or electronic means.

23. The method of claim 22, wherein the display superimposes the views.

24. An apparatus
for acquiring data from ultrasonic data with a two-dimensional B-scan probe, the apparatus comprising a processor configured for:
a) Coupling a probe to a sensor, with a means of reporting its position in real time relative to a base;
b) Displaying a generic body model and a set of fiducial points to be touched, in order;
c) Deriving, from the position of the probe at each of the touches, a transformation from coordinates relative to the base to the coordinates in which the body model is defined;
d) Deriving from the position of the probe at each of the touches an adjusted body model, with estimates of internal anatomical positions;
e) Displaying with the adjusted body model a volume containing a target tissue, in its estimated anatomical position;
f) Using the said estimates of internal anatomical positions to estimate the absorption between the probe and its target;
g) Using the said estimate of absorption to select the ultrasound frequency and amplitude for an optimal image;
h) Using the said estimates of internal anatomical positions to estimate the speed of sound at different locations in the body, obtaining an estimate of the relation of distance to echo time;
i) Displaying a 2D fan corresponding to the emitted sound rays in their current positions, relative to the body;
j) Showing in representative points of the said displayed volume containing a target tissue whether good data have been captured for that point;
k) Recording the good data for each such point, in each position of the 2D fan;
l) Assembling a volume data set from these 2D fans, filling the target volume; and
m) Transferring the said volume data set to a display accessed by a clinician.

* * * * *